(12) United States Patent
Veldhuizen et al.

(10) Patent No.: US 6,656,178 B1
(45) Date of Patent: Dec. 2, 2003

(54) VERTEBRAL-COLUMN FUSION DEVICES AND SURGICAL METHODS

(75) Inventors: Albert Gerrit Veldhuizen, Lagestukken 76, 9761 KS Elde (NL); Gert Nijenbannin, Oldenzaal (NL); Alec Paul Birkbeck, Leeds (GB); Gary Stuart Fenton, Leeds (GB); Martin Pfleiderer, Leeds (GB); Marc Sanders, Leeds (GB)

(73) Assignees: Baat B.V. Engineering, Hengelo (NL); Depuy International Limited, Leeds (GB); Albert Gerrit Veldhuizen, Elde (NL)

( * ) Notice: Subject to any disclaimer, the term of this patent is extended or adjusted under 35 U.S.C. 154(b) by 167 days.

(21) Appl. No.: 09/626,817

(22) Filed: Jul. 27, 2000

(30) Foreign Application Priority Data

Jul. 28, 1999 (NL) .............................. 1012719

(51) Int. Cl.$^7$ ................................. A61F 2/44
(52) U.S. Cl. ..................... 606/61; 623/17.11
(58) Field of Search ............... 606/61; 623/17.11, 623/17.13, 17.16

(56) References Cited

U.S. PATENT DOCUMENTS

| | | | |
|---|---|---|---|
| 4,665,906 A | 5/1987 | Jervis | 128/92 |
| 5,171,280 A | 12/1992 | Baumgartner | 623/17 |
| 5,609,637 A | 3/1997 | Biedermann et al. | 623/17 |
| 5,716,416 A | 2/1998 | Lin | 623/17 |
| 5,749,916 A | 5/1998 | Richelsoph | 623/17 |
| 5,836,948 A | 11/1998 | Zucherman et al. | 606/61 |
| 5,919,235 A | 7/1999 | Husson et al. | 623/17 |
| 5,964,770 A | 10/1999 | Flomenblit et al. | 606/78 |
| 5,976,187 A | 11/1999 | Richelsoph | 623/17 |
| 6,019,793 A | 2/2000 | Perren et al. | 623/17 |
| 6,117,174 A | 9/2000 | Nolan | 623/17 |
| 6,193,757 B1 | 2/2001 | Foley et al. | 623/17 |
| 6,238,397 B1 | 5/2001 | Zucherman et al. | 606/61 |
| 6,245,108 B1 | 6/2001 | Biscup | 623/17 |
| 6,488,710 B2 * | 12/2002 | Besselink | 623/17.15 |

FOREIGN PATENT DOCUMENTS

| | | | |
|---|---|---|---|
| EP | 0302179 A | 4/1988 | C05F/7/00 |
| EP | 0 773 008 A1 | 8/1995 | 2/44 |
| EP | 0 743 045 A2 | 4/1996 | 17/64 |
| EP | 0 743 045 A3 | 4/1996 | 17/64 |
| EP | 0 873 718 A2 | 4/1996 | 17/44 |
| EP | 0853932 A2 | 1/1998 | A16F/2/44 |
| EP | 0 916 323 A1 | 6/1998 | 2/44 |
| FR | 2 712 486 | 11/1993 | 2/44 |
| WO | WO 95/01763 | 1/1995 | 2/44 |
| WO | WO 98/17207 | 4/1998 | A16F/2/44 |
| WO | WO 98/56319 | 12/1998 | 2/44 |
| WO | WO 99/16385 | 4/1999 | A16F/2/06 |
| WO | WO 00/06962 | 2/2000 | F26B/15/12 |
| WO | WO 00/53126 | 9/2000 | A61F/2/44 |
| WO | WO 00/62719 | 10/2000 | A16F/2/44 |

* cited by examiner

Primary Examiner—Eduardo C. Robert
Assistant Examiner—David Comstock
(74) Attorney, Agent, or Firm—Kunzler & Associates

(57) ABSTRACT

A vertebral-column device that is suitable to be received in an intervertebral space between two dorsal vertebrae, the prosthesis comprising a curved strip of biocompatible material. The width of the strip being such that after placement, the strip makes contact with the vertebrae. The strip is manufactured from a material that can undergo great deformations before permanent deformation arises. The strip is curved in a shape in which the extremities are situated apart from one another and the radius of the curved parts and the thickness of the strip are chosen in such a way that when the strip is bent out into an approximately straight strip, scarcely any permanent deformation arises. Thus, the strip which has been bent out into an approximately straight strip is capable of being introduced into an intervertebral space where the strip assumes its original curved shape.

31 Claims, 7 Drawing Sheets

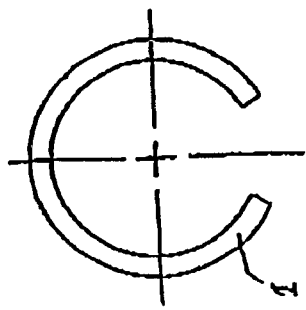
Fig 1a
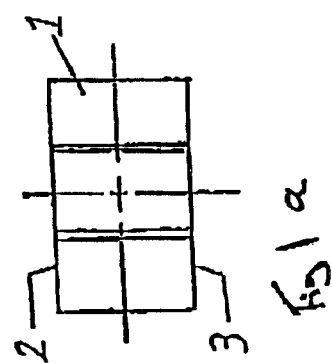
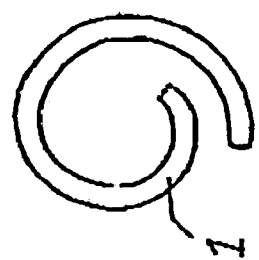
Fig 1b
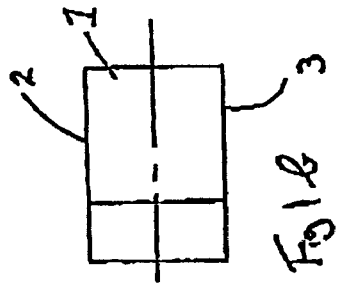
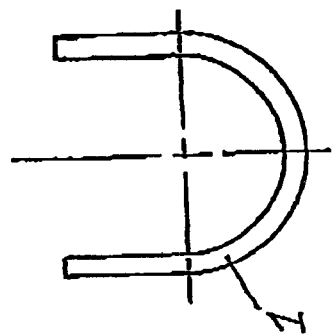
Fig 1c
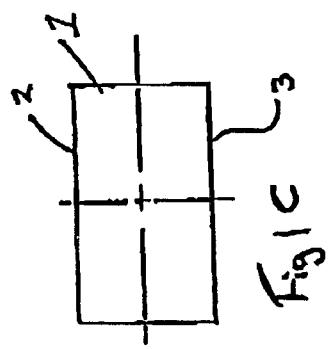
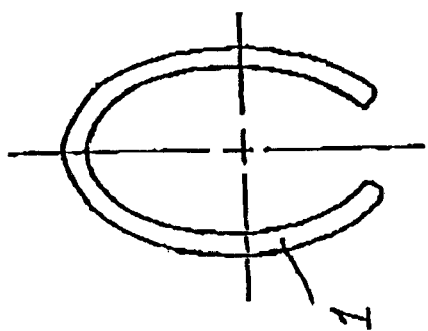
Fig 1d
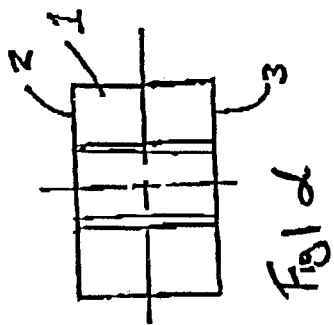
Fig 1

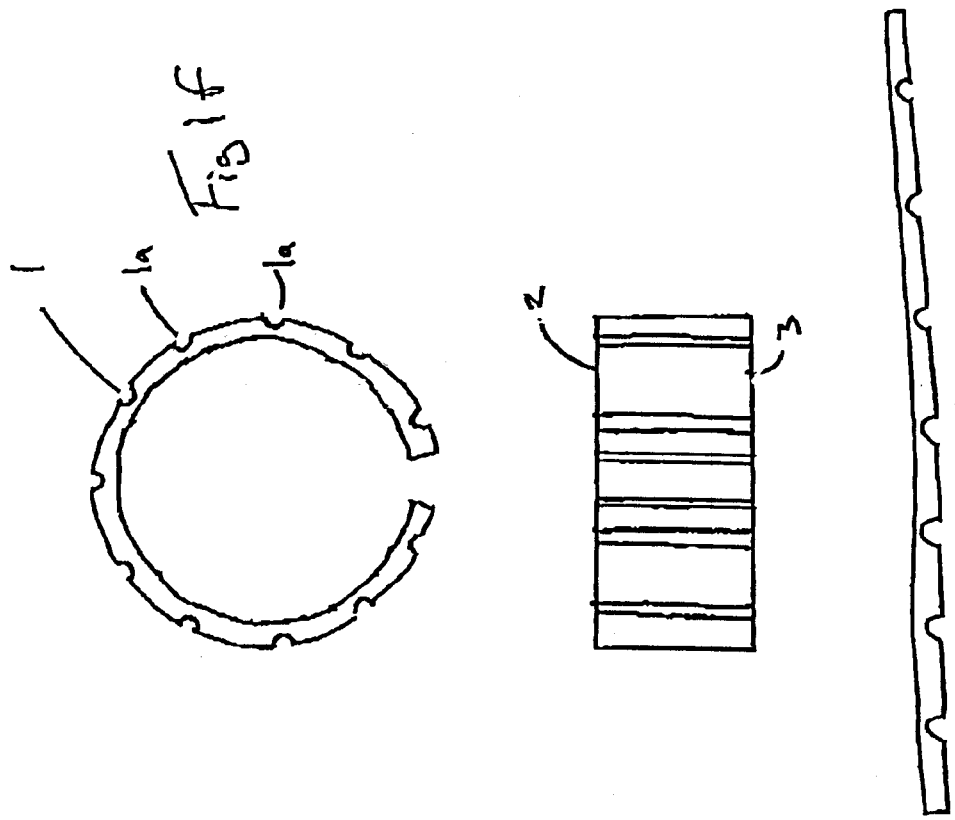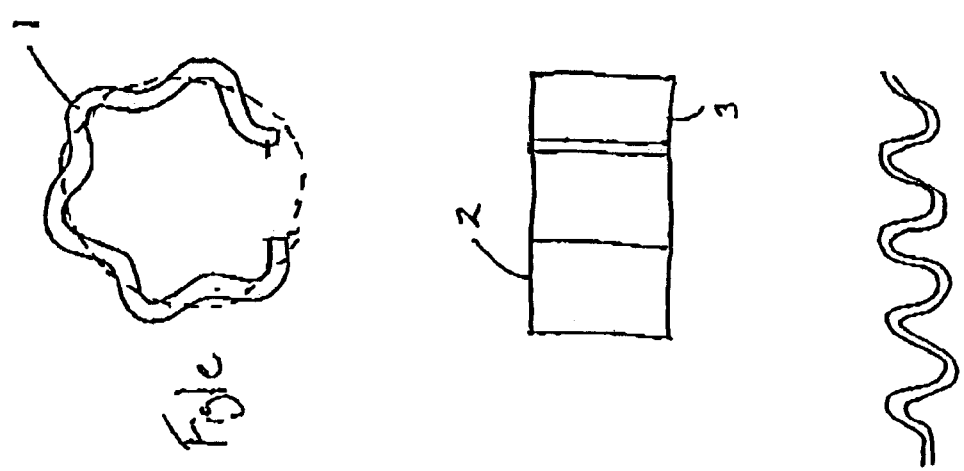

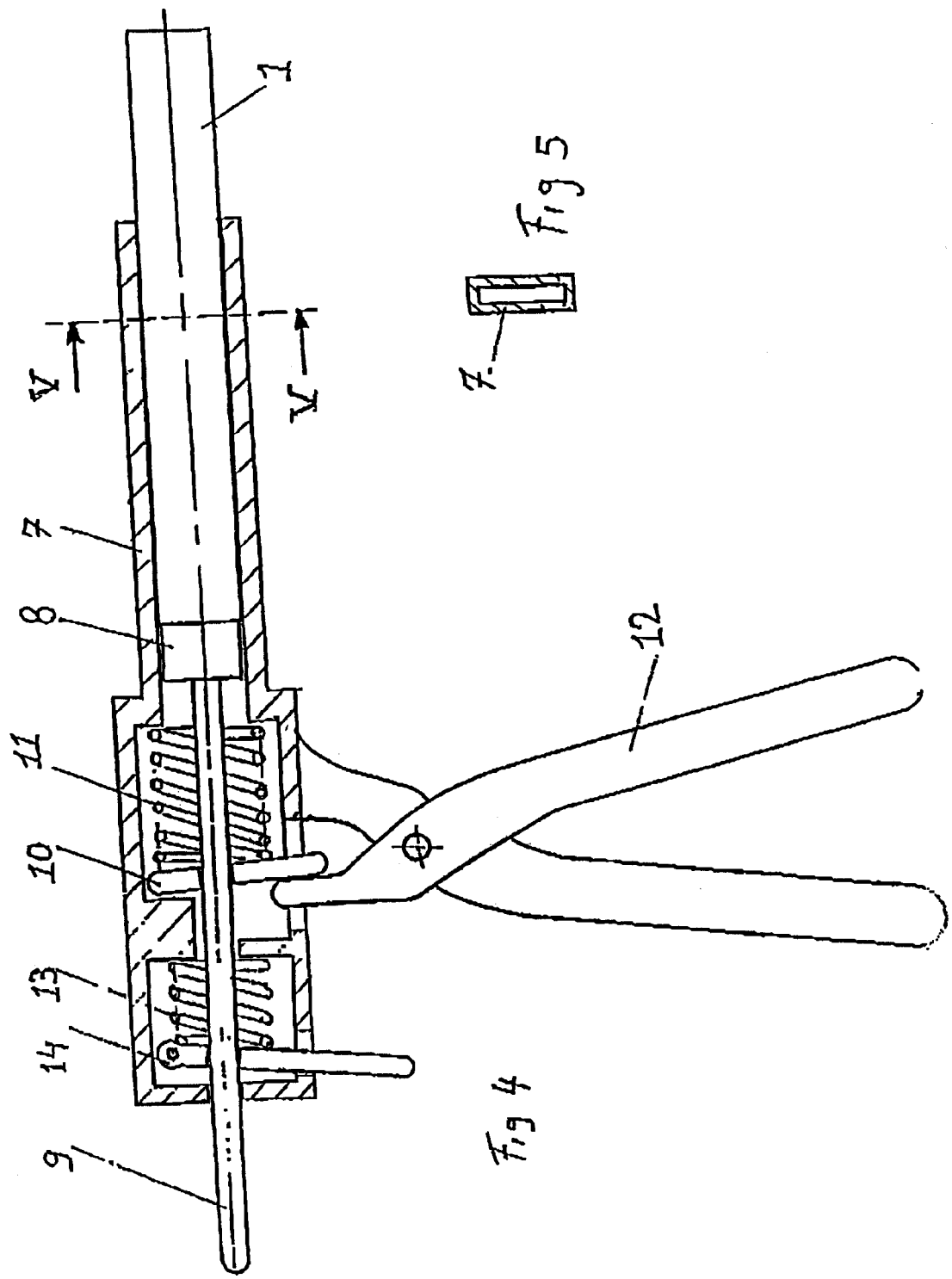

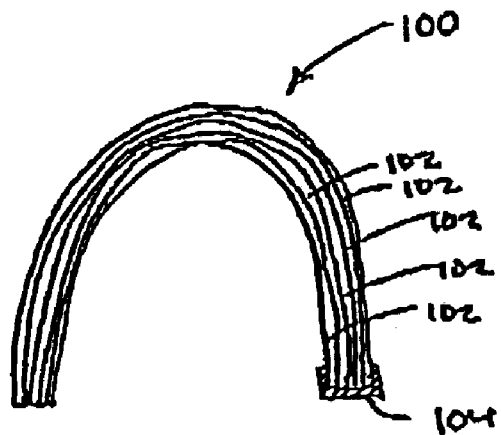
Fig 10
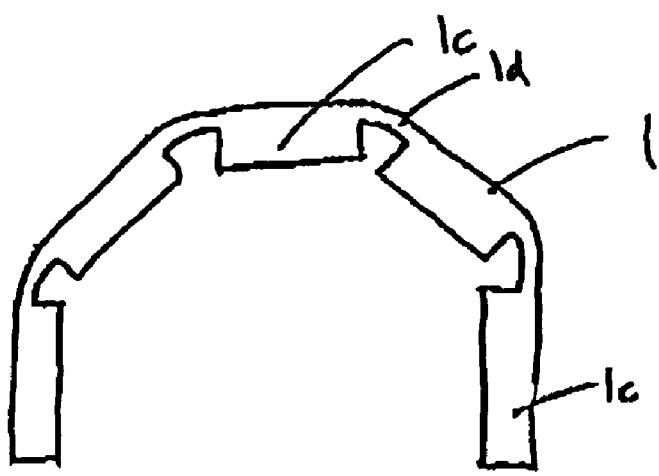
Fig 1g
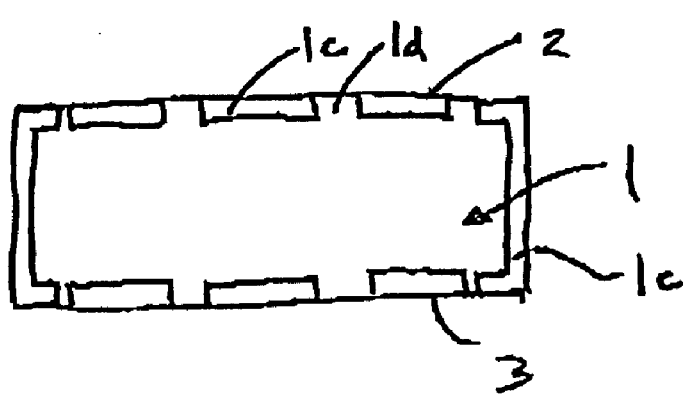

VERTEBRAL-COLUMN FUSION DEVICES AND SURGICAL METHODS

The invention concerns improvements in and relating to vertebral-column fusion devices, surgical apparatus and surgical methods. In particular, but not exclusively, the invention relates to a vertebral-column fusion device that is suitable to be received in an intervertebral space between two dorsal vertebrae, said fusion device comprising a curved strip of biocompatible material, with the width of the strip being such that after placement said strip makes contact with the aforementioned vertebrae.

Fusion devices aim to promote fusion of the adjoining vertebrae together. As such they are distinct from disc replacements where the new disc aims to mirror the behaviour of and to be given the mobility of the natural disc it replaces.

Fusion devices, in the most general sense, are known and are employed in cases where, as a result of accident, overloading, old age or otherwise, an intervertebral disc of the dorsal vertebral column is no longer able to perform its normal supporting and stabilising function. In these cases there is fitted in the space of said intervertebral disc a device which entirely or partially takes over the load-bearing function of the intervertebral disc until bone fusion has taken place. Known fusion devices of this type are constituted by a so-called cage construction with a closed peripheral surface which, for example, may have a cylindrical shape, and two end faces which after placement make contact with the two vertebrae bounding the intervening space. This type of fusion device is introduced into the intervertebral space by means of a surgical intervention and is maneuvered into a precise position. Moreover, for good stability and satisfactory load-bearing capacity it is usually necessary to fit two of these devices in the intervertebral space, side by side, one on each side of the vertebral column.

One disadvantage of these known devices is that they are difficult to fit in the intervertebral space, fitment being effected by means of a labourious, time-consuming and therefore expensive surgical intervention, in the course of which a relatively large access opening has to be made, with destabilisation and local trauma as a consequence. In the case of a posterior approach this is effected, as a rule, on the left and/or right sides of the spinal cord and in either case results in a fairly serious intervention.

The invention has amongst its aims to provide a better device that is simpler to fit in the intervertebral space and that, while preserving the simplicity of fitting, can nevertheless have a larger and therefore more favourable bearing surface than the known devices. The invention has amongst its aims to provide advantageous surgical apparatus for introducing devices into an intervertebral space. The present invention has amongst its aims to provide an advantageous surgical method for introducing a fusion device into an intervertebral space and/or for using surgical apparatus.

According to a first aspect of the invention we provide an intervertebral fusion device, the device comprising an elongate element, the elongate element providing one or more upper load bearing surfaces and one or more lower load bearing surfaces, the upper and lower load bearing surfaces being vertically spaced from one another by the elongate element, the elongate element having a first state and a second state, the elongate element having a substantially linear configuration in the first state and a less linear configuration in the second state, the elongate element being capable of transition, at least once, from the second state to first state and being capable of transition, at least once, from the first state to the second state, the elongate element being of shape memory alloy.

Preferably the intervertebral fusion device promotes fusion of one vertebrae to an adjacent vertebrae with the device there between. Fusion may be promoted by the ingrowth of bone or other material. The fusion device may restrain movement of one vertebrae relative to the other vertebrae the fusion device contacts.

The elongate element may be a substantially planar element, for instance a strip or sheet.

The elongate element may have a non-rectilinear cross-section at one or more locations along its length. The non-rectilinear cross-section may be provided throughout the length. The non-rectilinear cross-section may be provided at a plurality of locations along the length, with a rectilinear cross-section being provided at a location between two or more of those locations, ideally between each of those non-rectilinear cross-sections. The non-rectilinear cross-section may provide an increased thickness portion at the upper edge/upper load bearing surface and/or at the lower edge/lower load bearing surface of the elongate element. The non-rectilinear cross-section may be of a linear C-shaped cross-section. The portions of the elongate element having a non-rectilinear cross-section may have the same profile in the first and second states. The portions of the elongate element between the non-rectilinear portions may flex and/or bend during the change from first to second state and/or vice-versa.

The elongate element may be a mesh. The elongate element may be continuous or may have one or more holes or apertures in it. The holes may be round and/or oval and/or triangular and/or diamond shaped.

The elongate element may have a linear upper load bearing surface or surfaces. The elongate element may have a discontinuous upper surface. One or more indentations may be provided in the upper load bearing surface. The elongate element may have a serrated upper load bearing surface or surfaces. The elongate element may have one or more protrusions or spikes provided on the upper load bearing surface or surfaces. The upper surface of the elongate element may be defined by one or more, preferably linear, load bearing surfaces interspaced by one or more indentations. The indentations may be triangular in shape. The upper load bearing surface or surfaces of the elongate element may be provided with one or more protrusions or teeth. The protrusions or teeth may have a triangular profile.

The elongate element may have a linear lower load bearing surface or surfaces. The elongate element may have a discontinuous lower surface. One or more indentations may be provided in the lower load bearing surface. The elongate element may have a serrated lower load bearing surface or surfaces. The elongate element may have one or more protrusions or spikes provided on the lower load bearing surface or surfaces. The lower surface of the elongate element may be defined by one or more, preferably linear, load bearing surfaces interspaced by one or more indentations. The indentations may be triangular in shape. The lower load bearing surface or surfaces of the elongate element may be provided with one or more protrusions or teeth. The protrusions or teeth may have a triangular profile.

The upper and lower load bearing surface and/or one or more of the upper and lower load bearing surfaces may be parallel to one another. The upper and lower load bearing surface and/or one or more of the upper and lower load bearing surfaces may be angled relative to one another. The angle between a projection of the upper load bearing surfaces and/or at least one of the upper load bearing surfaces and the lower load bearing surface and/or at least one of the lower load bearing surfaces may be 5° to 15°, more preferably 7° to 13°. More preferably the angle is 8° to 12°, still more preferably 9° to 11° and ideally is 10°. One or both of the upper or lower load bearing surfaces may be non-perpendicular to the height of the elongate element.

The upper and/or lower load bearing surface or surfaces may contact and/or enter the vertebrae in use.

The vertical spacing of the upper and lower load bearing surface or surfaces may be between 7 mm and 20 mm, preferably between 8 mm and 17 mm and ideally between 9 mm and 15 mm. The maximum vertical spacing is preferably less than 22 mm, more preferably less than 19 mm and ideally less than 17 mm. The maximum vertical spacing is preferably provided at one or both ends of the elongate element, particularly when the device is introduced from the anterior side of the patient. The maximum vertical spacing is preferably provided within the middle portion of the elongate element, particularly when the device is introduced from the posterior side of the patient.

The minimum vertical spacing is preferably more than 4 mm, more preferably more than 5 mm and ideally more than 6 mm. The minimum vertical spacing is preferably provided at one or both ends of the elongate element, particularly when the device is introduced from the posterior side of the patient. The minimum vertical spacing is preferably provided within the middle portion of the elongate element, particularly when the device is introduced from the anterior side of the patient.

The first state may provide a linear configuration for the elongate element. The first state may provide a non-linear configuration, for instance a curve or waveform, for the elongate element. A non-linear configuration may mean one end of the elongate element being offset from a tangent to the other end by less than 5 mm, preferably less than 4 mm, more preferably less than 2 mm and ideally less than 1 mm. A non-linear configuration may mean one or more portions of the elongate element being disposed to one side or the other side, relative to a centre line of the elongate element. The one or more portions may be so disposed by one or curves, preferably alternating direction curves, ideally a waveform. The first state may provide a configuration in which one end of the elongate element is further, in a straight line, from the other end of the elongate element than any other component. The part of the elongate element intervening the two ends may be non-linear, for instance including one or more curves. A wave form consisting of alternating curves of opposing direction is particularly preferred.

The second state may provide a configuration in which at least a part of the elongate element is curved. The second state may provide a situation in which the entire length of the elongate element is curved. The curve may be of constant radius throughout the length of the elongate element. The curve may be a various radii over the length of the elongate element. The minimum radius is preferably at least 3 mm and more preferably 5 mm.

The second state may provide a configuration in which at least a part of the elongate element is curved and in which at least a part of the elongate element has a waveform and/or serpentine and/or wavy profile. The parts may be the same part of the elongate element. The curves forming the waveform may have a radius of less than 1 mm.

In the second state the elongate element may have a configuration which is a part circle and/or full circle and/or spiral and/or U-shape and/or a part oval and/or full oval. The ends of the elongate element may be touching or may be apart in the second state. One end of the elongate element may be tucked behind the other in the second state, touching or not touching Preferably the elongate element is formed of a single piece of shape memory alloy.

The shape memory alloy is preferably an alloy of titanium, most preferably with nickel. The shape memory alloy may be an alloy of copper and zinc and/or aluminium. The shape memory alloy may be an alloy of iron and nickel. The shape memory alloy may be an alloy of copper, aluminium and nickel. The alloys may include other elements.

The transition from second state to first state is preferably provided in the warm state for the shape memory alloy. The transition from the first to second state is preferably provided in the warm state for the shape memory alloy. The elongate element may be brought into in the cold state, prior to or during insertion and/or be in the cold state after insertion, at least temporarily. The transition from first state to second state may be caused by the elongate element passing from the cold state to the warm state in the patient. The passage from cold state to warm state may be caused by body heat and/or external heating.

The transition from second to first state is preferably achieved by the application of stress to the elongate element. The transition from first to second state is preferably achieved by the removal of the application of stress to the elongate element.

The shape memory alloy preferably undergoes pseudoplastic deformation during the transition from first to second state. The transition from first to second state preferably involves a strain of less than 10% for any part of the elongate element, more preferably the elongation is less than 8% for any part.

The elongate element preferably has a thickness, for instance perpendicular to the vertical in use, of less than 2 mm and more preferably of less than 1.5 mm. A thickness of between 1 mm and 1.5 mm is preferred.

The elongate element may have a constant thickness throughout its length and/or width. The elongate element may be provided with one or more reduced thickness portions. The reduced thickness portion or portions may be provided by recesses and/or notches and/or grooves in the elongate element. Preferably the surfaces defining the elongate element and feature defining the reduced thickness portion are connected by rounded surfaces. The reduced thickness portion may have an extent along the elongate element at that reduced thickness. The feature defining the reduced thickness portion may include a curved portion linking the elongate element at normal thickness to the elongate element at reduced thickness, with a further curve linking the reduced thickness to the normal thickness of the elongate element. Preferably the feature defining the reduced thickness portion is provided on the outside surface of the elongate element. The feature defining the reduced thickness portion preferably extends throughout the width of the elongate element. The features defining the reduced thickness portion may be regularly spaced along the length of the elongate element. The features defining the reduced thickness portion or portions may be irregularly spaced along the length of the elongate element. In particular, the features defining the reduced thickness portion may be preferentially provided in the portion of the elongate element which undergoes the greatest change, even the change, in profile between the first and second state. The features defining the reduced thickness portion may be less frequently provided or absent from the portion or portions of the elongate element undergoing least or no change in profile between the first and second state.

Where the elongate element includes one or more reduced thickness portions and/or one or more enhanced thickness portions, it is preferred that the elongate element have a minimum thickness, in the reduced thickness portions, of at least 0.4 mm. It is preferred that the elongate element has a maximum thickness, in the non-reduced thickness portions, or enhanced thickness portions of at most 3 mm.

The maximum extent of the elongate element, measured from any point to any other in a straight line, is preferably less than 50 mm, more preferably less than 40 mm and ideally less than 35 mm. The maximum extent of the elongate element, measured from any point to any other in a straight line, is preferably at least 7 mm, more preferably at least 10 mm and ideally at least 12 mm.

One or both ends, preferably only the trailing end during insertion, of the device may be provided with an engagement profile. the engagement profile is preferably used to link the device to a surgical instrument, particularly a surgical instrument for inserting the device. the engagement profile preferably provides an engagement with the instrument during insertion and/or removal and/or manipulation and/or advancement and/or retraction of the device.

The engagement profile preferably provides one or more surfaces, at least in part, facing away from the other end of the device. Such a surface may provide an abutment surface during insertion. The engagement profile preferably provides one or more surfaces, at least in part, facing the other end of the device. Such a surface may provide an abutment surface during retraction and/or manipulation.

The engagement profile may include a surface extending from the end of the device, a second surface extruding from the end of the device and a third surface linking the two. The third surface may be generally parallel to the end of the device. The first and second surfaces are preferably non-perpendicular to the end of the device and/or non-parallel to one another. The engagement profile may define a protruding dovetail from the end of the device, ideally defined by the first, second and third surfaces.

The engagement profile may include a recess in the device defined by a first surface extending into the device, a second surface extending into the device and a third surface linking the two. The third surface may be generally parallel to the end of the device. The first and second surfaces are preferably non-perpendicular to the end of the device and/or non-parallel to one another. The engagement profile may define a recessed dovetail, ideally defined by the first, second and third surfaces.

The invention may be a vertebral-column device/prosthesis, suitable to be received in an intervertebral space between two dorsal vertebrae, said prosthesis comprising a curved strip of biocompatible material and the width of said strip being such that after placement said strip makes contact with the aforementioned vertebrae, characterised in that the strip is manufactured from a material that can undergo great elastic deformations before permanent deformation arises, and the strip is curved in a shape in which the extremities are situated apart from one another and the radius of the bent parts and the thickness of the strip are chosen in such a way that when the strip is bent out into an approximately straight strip scarcely any permanent deformation arises, whereby the strip which has been bent out into an approximately straight strip is capable of being introduced into an intervertebral space where the strip assumes its original curved shape.

The strip may be manufactured from a shape memory alloy/memory material, such as an alloy of titanium and nickel, which can undergo great deformation before permanent deformation arises.

The curved strip may have a U-shape. The curved strip may have a circular shape. The curved strip may have a spiral shape. The strip may have an oval shape.

The strip may have a thickness of 1.5 mm and the curved parts of the strip exhibit a radius of at least 12.5 mm. Where the minimum thickness of the elongate element is less than 1.5 mm, for instance, less than 1 mm, the curved parts of the strip may exhibit a radius of at least 8 mm.

The strip may be provided with holes. The strip may have a gauze structure.

The strip may have provided on its sides with projections which after the strip has been fitted in the intervertebral space come into contact with the two vertebrae bounding said space and fix the strip with respect to them.

According to the invention the device exhibits the characteristic that the strip is manufactured from a material that can undergo great deformations before permanent deformation arises, and the strip is curved in a shape in which the extremities are situated apart from one another and the radius of the curved parts as well as the thickness of the strip are chosen in such a way that when the strip is bent out into an at least approximately straight strip scarcely any permanent deformation arises, in which case the strip which has been bent out into an approximately straight strip is capable of being introduced into an intervertebral space where the strip assumes its original curved shape.

The material of the strip may, moreover, be constituted by a shape memory alloy/memory material such as an alloy of titanium and nickel. Such a material has, besides its advantageous property that it delivers virtually constant force in the course of progressive deformation, the additional property that it can undergo very great deformations of up to 6% to 8% without the material deforming permanently.

In the case of the devices according to the invention, optimal use is made of the aforementioned properties by giving the strip such a curved shape that crosscut edges are obtained which form a bearing surface of the desired dimension for the vertebrae. Moreover, the curves of the strip are given a radius such that, given the thickness of the strip which arises when the strip is bent out into a straight strip, scarcely any or no permanent deformations arise—that is to say, the deformations remain below the order of 6% to 8% straight can easily be inserted via a narrow slit-shaped incision into the intervertebral space where the strip then reassumes its original curved shape. Because the curved strip can have crosscut faces of substantial dimension in comparison with the crosscut faces of known devices, with the device according to the invention it is possible to use only one device which provides satisfactory load-bearing strength and stability in an intervertebral space. In this way the fitting of the device becomes simpler, because only one small opening is necessary for the insertion, causing less trauma. Depending on circumstances, the strip according to the invention can be curved in a U-shape, a circular shape, a spiral shape, a rectangular shape or any other desired shape. Another favourable design of the device according to the invention exhibits the characteristic that the strip has a thickness of 1.5 mm and the curved parts exhibit a radius of at least 12.5 mm. In this way it is ensured that when the strip is bent out into an almost straight strip the deformation of the strip in the curved parts remains below 8%, so that no permanent deformation or scarcely any permanent deformation arises and the strip reassumes its original curved shape after its introduction into the intervertebral space.

In order to promote a successful ingrowth and accretion of bone, according to a further embodiment of the devices according to the invention the strip is provided with holes or the strip is designed in the form of a gauze.

In order to fix the device well in its place after fitment in the intervertebral space, according to a further embodiment the strip is provided on its sides with projections which come into contact with vertebrae bounding the space and consequently oppose a displacement with respect to them.

According to a third aspect of the invention we provide a method of surgery, the method including the acts of:

making an incision in the patient;

removing at least part of an intervertebral disc from the patient through the incision, thereby providing an intervertebral disc space; and inserting a device into the intervertebral space;

the device comprising an elongate element, the elongate element providing one or more upper load bearing surfaces for a vertebrae and one or more lower load bearing surfaces for a vertebrae, the upper and lower load bearing surfaces being vertically spaced from one another by the elongate element, the elongate element having a first state prior to insertion and a second state after insertion, the elongate element having a substantially linear configuration in the first state and a less linear configuration in the second state, the elongate element undergoing transition, from the first state to the second state within the patient, the elongate element being of shape memory alloy.

The device may have any of the features, options or possibilities set out elsewhere in this document, including the first and/or second and/or sixth aspects of the invention.

The incision may be made anteriorally and/or posteriorally. Preferably the incision is less than 5 cm long, more preferably less than 3 cm long.

Preferably at least the nucleus pulposus is removed. The annulous fibrosis and/or vertebral end-plate may also be removed.

The device may be inserted using surgical apparatus. The surgical apparatus may be provided as detailed in the fourth and/or fifth aspects of the invention and/or as described elsewhere in this document.

Whilst only a single device may be inserted in the intervertebral space between any two vertebrae, a plurality of devices may be inserted. Two or more devices may be inserted into a position where they are alongside one another. Two or more devices may be inserted into a position where at least a part of one of the devices is enclosed by one of the other device's and/or lies within the outline of one of the other device's. Two or more devices may be inserted such that an opening defined between the two ends of one of the device's is opposed by at least a part of another device. Bone graft material may be provided within the outline of one or more of the devices. Bone graft material may be provided between at least a portion of one device and at least a portion of another device.

In the method the end of the apparatus, particularly the end of the holding frame, may be inserted into the incision and ideally between the vertebrae. The apparatus is preferably inserted in one orientation and rotated to a second orientation after insertion. The second orientation may be between 70 and 110° of the first. Preferably the end of the apparatus abuts the opposing vertebrae during rotation. Preferably continued rotation increase the separation of the opposing vertebrae. In this way easier access to the vertebral space may be gained.

The insertion of the device may cause the transition from first to second state, particularly where the restraining force is removed by insertion. The transition from first to second state may occur after insertion of the device, particularly where the transition is caused by the device passing from cold state to warm state. The passage of the device from cold to warm state is preferably at least in part be caused by warming due to the patient's body heat. Additional heating for the device may be provided, particularly external heating. The temperature of the device may be raised to at least 40° C. and ideally to between 40° C. and 50° C. by external heating.

The method may include the ingrowth of bone or other material to complete the fusion after insertion.

The method may include retraction of the device. The method may include manipulation of the device. Preferably manipulation and/or retraction and/or insertion are provided using surgical apparatus according to the fourth or fifth aspects of the invention and/or by means of a profile on the end of the device as provided in the second aspect of the invention.

The method may include retraction of the device into the apparatus. The method may include retraction of the device so as to cause the device to change from the second state into the first state. The method may include the retraction of the device into the surgical apparatus.

The present invention also relates to apparatus that is suitable for the insertion of a device as described above into an intervertebral space.

According to a fourth aspect of the invention we provide surgical apparatus for inserting a device into a patient, the apparatus including a holding frame for the device, a pushing element configured to enter the holding frame, at least one hand operated component, the hand operated component being indirectly or directly linked to the pushing element, operation of the hand operated component advancing the pushing element into the holding frame.

The device may be as described in the first and/or second aspect of the invention.

The holding frame preferably extends along an axis. The cross-section of the holding frame perpendicular to the axis is preferably constant. Preferably the holding frame has an axial extent greater than the device, particularly relative to the first state for the device mentioned above. The holding frame is preferably continuous. The holding frame may be tubular. The tubular form may have a circular cross-section, but preferably has a rectilinear cross-section. The rectilinear cross-section may be between 1 and 20% greater than the cross-section of the elongate element in the height direction. The rectilinear cross-section may be between 1 and 10% greater than the cross-section of the elongate element forming the device in the thickness direction. The holding frame may be between 1 and 25% longer than the device in the length direction.

The length direction for the device may be its elongate direction and/or longest dimension. The thickness direction for the device may be perpendicular to its elongate direction and/or its smallest dimension. The height direction for the device may be perpendicular to its elongate direction and/or its intermediate dimension of the three.

The holding frame may be sealed at one or both ends. Preferably the holding frame is sealed. The holding frame may be sealed by seals, preferably the pushing element breaks the seal when advanced in to the holding frame. Preferably the device breaks the seal when advanced out of the holding frame.

The holding frame is preferably detachable from the apparatus. The detachable holding frame may be fully sealed prior to use. Preferably the interior of such a holding frame is sterile prior to use. The detachable holding frame may be disposable or reusable.

The apparatus may have a body. The body may provide a mount for the holding frame and/or at least one hand operated component and/or pushing element.

The pushing element may have a cross-section substantially corresponding to the cross-section of the device and/or the holding frame.

The pushing element may be mounted on a rod, shaft or other elongate element, particularly one end thereof.

The pushing element may advance the device by abutting the device and/or by engaging the device.

The pushing element may be retractable. Preferably the pushing element engages the device and facilitates retraction thereof. The engagement for the device may be provided by a profile in the pushing element. The profile may be a recess, slot or aperture. Preferably the profile cooperates with a portion of corresponding profile on the device. Preferably the profile provides one or more abutments between the pushing element and the device during advancement and/or retraction and/or manipulation. The profile may correspond and/or cooperate with a device profile as defined in the second aspect of the invention.

The at least one hand operated component may be pivotally mounted on the apparatus body and/or on a protrusion therefrom. The protrusion may be hand held in use. The at least one hand operated component preferably abuts on a driving element when operated. The at least one hand operated component preferably advances the driving element towards the holding frame when operated. The driving element preferably advances the pushing element and/or a mounting therefore towards the holding frame when operated. The driving element may have an aperture through which the mounting for the pushing element passes. The driving element preferably catches on the mounting when advanced towards the holing frame. The driving element may be biassed away from the holding frame, for instance by a spring within the body. Preferably the driving element passes over the mounting when driven back away from the holding frame. The body may provide a restraining element. Preferably the restraining element resists movement of the pushing element and/or mounting therefore away from the holding frame. Preferably the restraining element is biassed, ideally by a spring, away from the holding frame. The restraining element may be attached to the spring. Preferably the restraining element allows free movement of the pushing element or mounting therefore towards the holding frame.

According to a fifth aspect of the invention we provide apparatus suitable for introduction of the prosthesis according to one or more of the preceding claims into an intervertebral space, characterised in that the apparatus comprises an elongated tubular body with a receiving space for a strip which has been bent out in elongated manner, said apparatus being further provided with means for exerting a force on said strip for pressing the strip out of the receiving space into an intervertebral space.

The apparatus may have receiving space has a rectangular shape in cross-section.

The apparatus may have the means for exerting a pressing-out force on said strip are constituted by a rod, one end of which is provided with a part which enters into contact with the strip, said rod being guided within a wall bounding the receiving space, said rod being displaceable in stepwise manner in the direction of the receiving space by means appropriate for this purpose and being arrested in the other direction by a blocking mechanism which is capable of being cleared after the strip has been introduced, after which the rod can be removed from the receiving space. In the invention said apparatus may comprise an elongated tubular body with a receiving space for a strip which has been bent out in elongated manner, said apparatus being further provided with means for exerting a force on said strip for pressing the strip out of the receiving space into an intervertebral space.

Moreover, according to a preferred embodiment the cross-section of the receiving space is rectangular and the means for pressing the strip out are designed in such a way that pressing-out proceeds in stepwise manner.

According to a sixth aspect of the invention we provide an intervertebral fusion device, the device comprising an elongate element, the elongate element providing one or more upper load bearing surfaces and one or more lower load bearing surfaces, the upper and lower load bearing surfaces being vertically spaced from one another by the elongate element, the elongate element having a first state and a second state, the elongate element having a substantially linear configuration in the first state and a less linear configuration in the second state, the elongate element being capable of transition, at least once, from the second state to first state and being capable of transition, at least once, from the first state to the second state, the elongate element being formed of a plurality of elongate components which at least in part extend alongside one another.

The elongate element may be provided with a plurality of elongate components which contact one another over at least a part, preferably all, of their length. The elongate components may correspond to one another in form. The elongate components may be of matching form. The elongate components may be equivalent to one another. Three, four or five elongate components may be provided. The elongate components may be in the form of a plurality of equivalently configured strips, adjacent strips being in contact with one another.

The elongate components are preferably connected together to form a single elongate element. The elongate components are preferably connected together at one end, particularly the end which is inserted first into the patient. The elongate components may be connected together by one or more fastenings. The elongate components may be joined together by one or more adhesive components.

This aspect of the invention may include for its device any of the features, options or possibilities set out elsewhere in this document.

The invention will now be described by way of example only, and with reference to the accompanying drawings, in which:

FIGS. 1a, b, c, d, e, f and g each show schematically, in two mutually perpendicular views, a shape of a device according to various embodiments of the invention;

FIG. 4 shows in cross-section, schematically and not to scale, one embodiment of an apparatus for inserting a device according to the invention into an intervertebral space;

FIG. 5 shows a cross-section of the apparatus end according to FIG. 4 along line V—V;

Figure 6A:
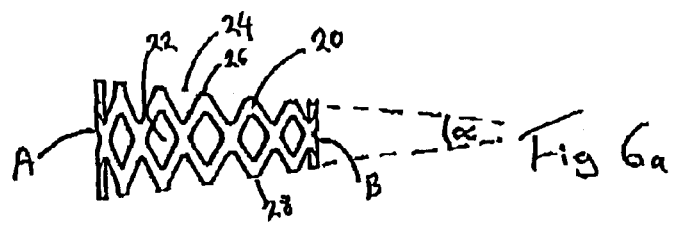
Figure 7:
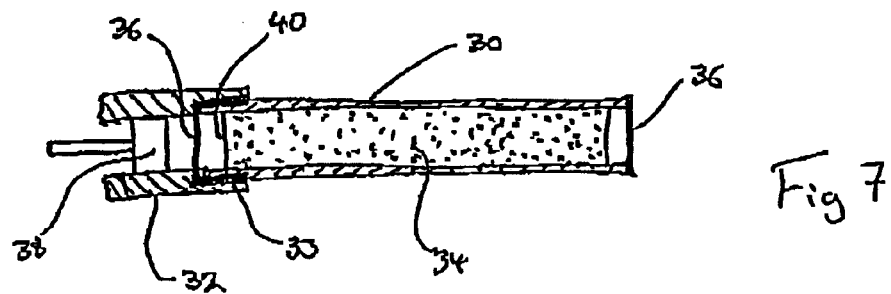
Figure 8:
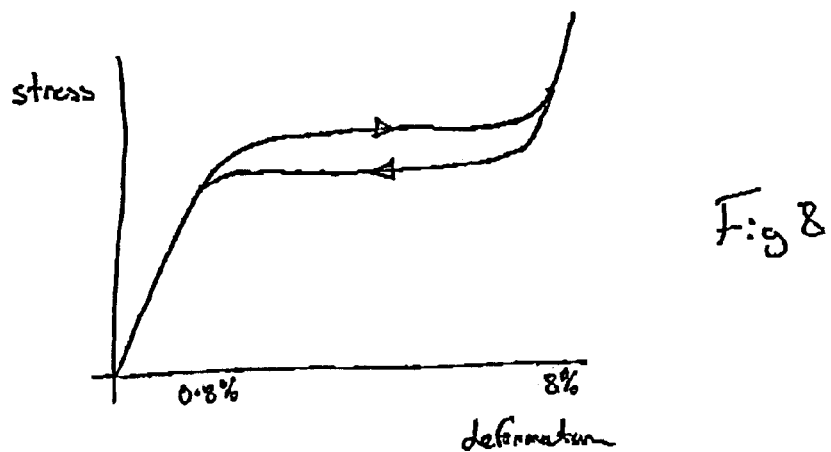
Figure 9A:
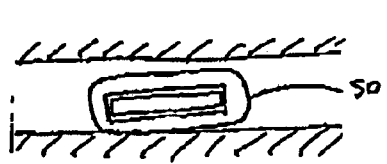
Figure 9B:
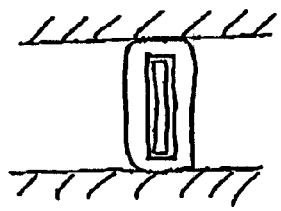
Figure 11A:
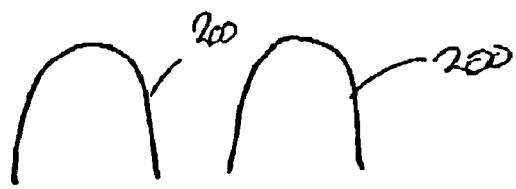
Figure 11B:
Figure 11C:
Figure 12:
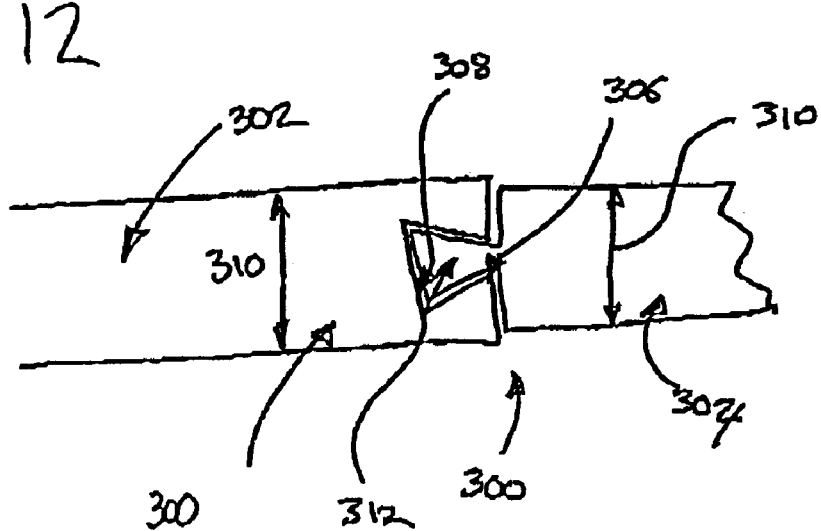

FIGS. 6a and b illustrate two further embodiments of devices according to the invention;

FIG. 7 illustrates an alternative embodiment of apparatus for inserting a device according to the invention into an intervertebral space;

FIG. 8 illustrates the elongation with stress behaviour of memory metals during deformation and relaxing;

FIG. 9a shows a partial view of two vertebrae and the end of an apparatus for dispensing a device according to the invention in the position in which it is initially inserted;

FIG. 9b shows the partial view of FIG. 9a with the apparatus rotated to the position in which the device is dispensed;

FIG. 10 shows schematically an alternative device according to an alternative form of the present invention;

FIGS. 11a, 11b and 11c show three different situations in which a pair of devices according to the invention are inserted between a pair of vertebrae; and FIG. 12 illustrates a detail of one end of a device according to yet another embodiment of the present invention.

In FIG. 1a a device according to the invention is shown in the form of a strip 1 of shape memory alloy, commonly known as memory material or metal, which exhibits a circular shape.

In FIG. 1b a device is shown consisting of a strip 1 of memory material which has a spiral shape.

In FIG. 1c a device is shown which comprises a strip 1 of memory material which has a U-shape.

In FIG. 1d a device is shown with a strip 1 of memory material which has the shape of an oval.

In FIG. 1e a device is shown with a strip 1 of memory material which has an overall partial circular form, but in which the strip is also provided with a waveform along its length. The strip thus extends beyond and within, alternately, the dotted line circular profile. One of the key features for such a form of the device is that the thickness of the material at any point is not increased (thus maintaining flexibility) whilst the overall length of material inserted in a given location is increased. This in turn increases the surface area of the top and bottoms of the strip which are available to support the vertebrae in use. Equivalent bearing surfaces can effectively be provided, using such a profile, to a device as illustrated in FIG. 1a, for instance, but with a thinner strip of material being used. The waveform also provides enhanced flexibility. Good flexibility for the device to ease insertion and good support capability for the device once positioned are thus both ensured. Such device forms may also be beneficial in the stored state, prior to use, where lower constraining forces may be needed to keep the device in the form ready for dispensing; in this case a waveform extending linearly as shown in the bottom of the three views of FIG. 1e.

In FIG. 1f again a device is shown in the form of a strip 1 of memory material which has a circular form. In this case the strip has a series of notches 1a in its external surface. The notches 1a have a maximum depth, into the thickness of the strip, of around 50% the thickness of the strip. The notches 1a extend across the full width of the strip in substantially the same profile and are evenly spaced along the length of the strip. The notches 1a in such a device provide locations to preferentially accommodate the deformation of the strip in the pre-dispense form. The remainder of the strip provides a significant thickness, and hence top and bottom surface areas, to achieve the desired level of support for the vertebrae they contact in use. Again a successful balance of flexibility to allow insertion and support area to maintain the separation of vertebrae is provided. The bottom illustration of the three in FIG. 1f shows the device in its linear profile, suitable for dispense.

In FIG. 1g another strip 1 is illustrated, on this occasion with a non-rectilinear cross-section in certain parts 1c. In these parts 1c the top and bottom load bearing surfaces of the strip 1 are extended. Between the expanded parts are rectilinear cross-sectioned parts 1d. It is at these parts 1d that most of the bending occurs during the transition from the first to second state and vice-versa. This linear C-shaped cross-section offers expanded support capability through increased bearing area, but still maintains flexibility.

The strip 1 of the foregoing figures is manufactured from a shape memory alloy which is constituted by an alloy of copper and zinc or titanium and nickel or nickel and iron. Shape memory alloys, due to their pseudo-plastic behaviour, has the property that it can undergo deformations of up to 8% before it exhibits permanent deformations. By giving a strip of this material a thickness and radii of curvature so that in the course of its being bent out into a straight strip no deformations of more than 8% arise, such a strip will reassume its original curved shape after being bent out into a straight strip and subsequently released.

In practice, therefore, the devices according to FIGS. 1a, b, c, d, e, f and g can be manufactured from a strip with a thickness of ideally 1.5 mm and the radii of curvature of the curved parts are ideally greater than 12.5 mm where a uniform thickness of strip is used. In the cases where reduced thickness portions are provided for the strips, the thickness could be considerably thinner, for instance down to 0.4 mm, at those reduced thickness locations. The radius of curvature may also be less in such cases, for instance greater than 8 mm. In this way, these strips will always resume their original shape after being deformed. This means that, after being deformed into an almost straight strip, such devices can be introduced, via a narrow slit made in the spine bounding the intervertebral space, into said intervertebral space where they then resume their original shape. In that position the end faces 2 and 3 then come into contact with the adjacent vertebrae, in which case the strip then performs a supporting and stabilising function for these vertebrae and thus takes over the load-bearing function of the intervertebral disc until bone fusion has come about. By virtue of the fact that the overall transverse dimension of this type of device can be fairly large, it is possible for the fitting of only one prosthesis to suffice.

Figure 2:
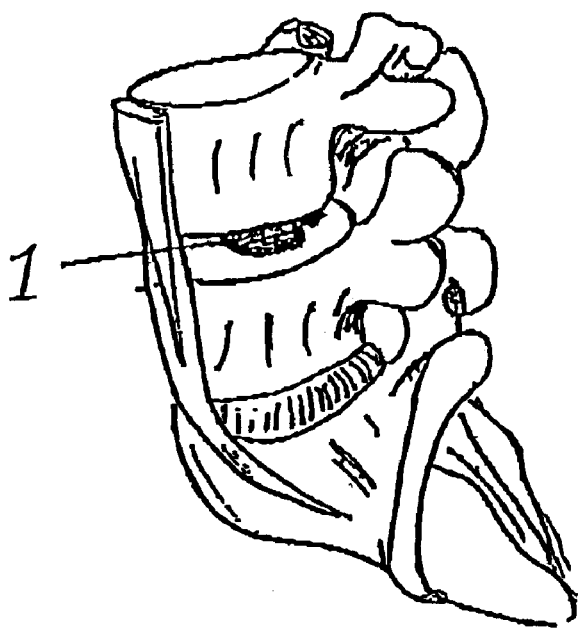
FIG. 2 shows, schematically and not to scale, an example of a vertebral column with a device according to the invention received therein.

An example of a device of the type according to the invention which is fitted in the intervertebral space of a vertebral column is shown schematically in FIG. 2.

Figure 3:
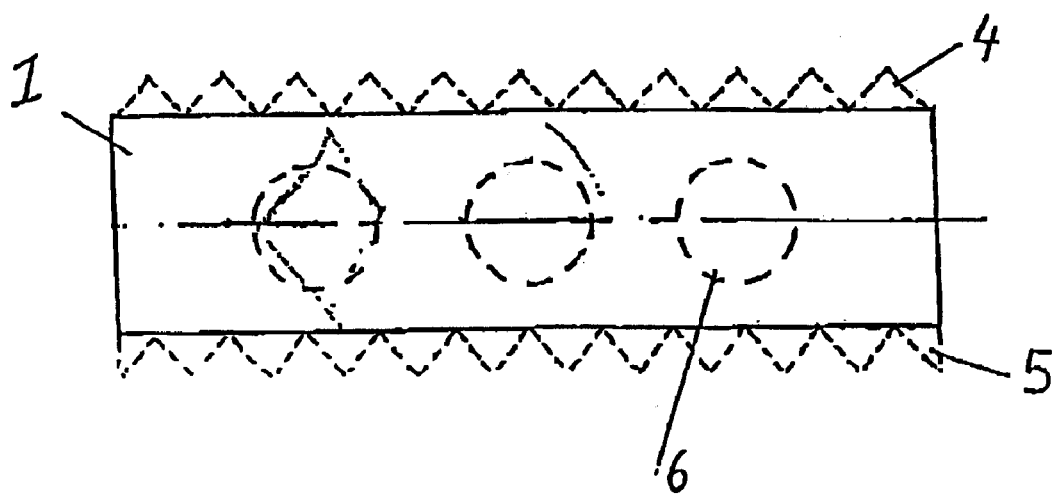
FIG. 3 shows schematically a further embodiment of the invention and comprising a bent-straight strip of a material, preferably memory material, which can undergo great deformations before permanent deformation arises.

A strip 1 in the deformed state, is shown in FIG. 3, wherein it is further indicated that such a strip may possibly also be provided with edges 4 and 5 which are not smooth but serrated. These serrated edges ensures that after placement of the device the latter remains well-positioned with respect to the vertebrae making contact with it. The strip may possibly also be provided with holes 6 which promote the ingrowth and accretion of bone.

For introduction of the strip 1, use may be made of apparatus according to FIG. 4. Said apparatus comprises a tubular part 7 which, as shown in FIG. 5, has a rectangular cross-section in which a strip 1, which has been deformed straight, can be received. On the end of the strip there rests a pressing-out block 8 which is provided on a long rod 9. Fastened to the rod 9, with some clearance, is a plate 10, whereby a spring 11 which presses said plate against one end of a rotatable operating lever 12 acts on one side of said plate. On the other side of the lever a spring 13 which presses a blocking lever 14 into its blocking state is fitted in the apparatus.

The operation of the apparatus is as follows. By pressing the plate 10 to the right with the lever 12 said plate will tilt and thereby be locked onto the rod 9, which is moved to the right by further movement of the lever 12, as a result of which the block 8 will press the strip 1 outwards. By now moving the lever back to the left, the plate 10 will also move back with it. Moreover, the rod 9 remains in its place by virtue of the fact that movement thereof to the left is blocked by the blocking lever 14. In this way, by moving the lever 12 back and forth a number of times, the strip 1 will be pressed in stepwise manner out of the receiving tube 7 into an intervertebral space, for example. After the strip has been pressed out of the tube, the block 8 and the rod 9 can be brought back into their initial position by pressing on the blocking lever, as a result of which the blockage is cleared and the rod with the block 8 can be moved to the left.

Figure 6B:
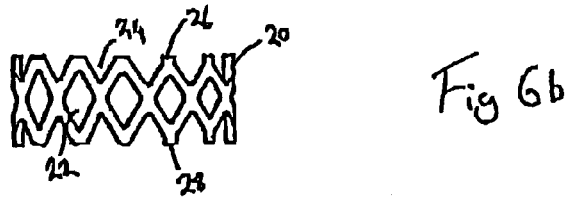

Further potential embodiments for the device are illustrated in FIGS. 6a and 6b. In FIG. 6a a strip 20 of material is provided with apertures 22 in the solid wall of the strip and indentations 24 in the upper and lower surface of the strip. The indentations 24 leave an upper load bearing surface 26 and lower load bearing surface 28 which due to their reduced surface area offers resistance to movement of the strip relative to the vertebrae. In the FIG. 6a embodiment the strip is of greater height on one side of the curve (side A in FIG. 6a) compared with the other side of the curve (side B in FIG. 6a). In effect side B is the location on the strip where the opening between the two ends is provided. The different heights for the strip at different locations and a gradual tapering between the two on both upper and lower load bearing surfaces provides a closer match between the device and the attitude of the vertebrae in practice. The angle, $\propto$, defined by a projection of the upper and lower surfaces, may be between 8 and 12° and is preferably 10°.

A similar embodiment of the device is illustrated in FIG. 6b, but in this case the upper and lower load bearing surfaces are parallel to one another.

It is highly desirable that the device is formed of a single layer of material as this avoids the risk of delamination, relative movement or other issues which arise with multi layer materials. Strips of between 1 and 1.5 mm in thickness can be used to provide sufficiently resilient devices which are capable of being straightened to a linear profile. A radius of approximately 15 mm is preferred to effect a suitable fusion device using a single device.

It is preferred that the device is relatively flexible to forces exerted in the plane of the intervertebral space/intervertebral disc. It is preferred, however, that the height of the device and/or the height of the separation between vertebrae it maintains does not vary.

In the alternative embodiment of the apparatus illustrated in FIG. 7, the permanent barrel of the FIG. 4 embodiment is replaced by a disposable tube 30 which can be releasably fastened on to the end of the apparatus 32 by screw threaded portions 33. The device 34 is provided within the tube 30 and is sealed at both ends by barriers 36. The device 34, therefore, is provided to the apparatus in a fully sealed manner which maintains it sterile during transport and dispensing.

In use, in a similar manner to the description above for the FIG. 4 embodiment, the piston 38 is advanced in the apparatus and pushes through the barrier 36 to contact the end 40 of the device 34 as a result. Continued advancement of the piston 38 pushes the device 34 forward and causes it to rupture the barrier 36 and thereafter pass into the intervertebral space.

The use of shape memory alloys, including memory metals, is advantageous during the dispensing process. Whilst the walls of the tube containing the device are used to restrain it during dispensing, once clear of the end of the tube the device begins to resume its original profile. The pseudo-elastic properties of memory metal materials, as illustrated in FIG. 8, mean that there is a "delay" in the shape memory alloy resuming its configuration as the stress is removed. Because of this, shape memory alloys are far easier to dispense using such apparatus than other materials which would immediately return to their original configuration upon removal of the stress. The applicability of the invention is not dependant on this possibility.

To insert devices according to the present invention, a small incision is made and the disc in the intervertebral space for which fusion is to be effected is removed. The size of the incision is minimised to minimise surgical trauma. Subsequent to the disc's removal the end of the apparatus for dispensing the device is inserted into the aperture through which the disc has been removed. The end of the device is inserted with the device in a substantially flat orientation, see FIG. 9a and is slowly rotated about its length to the orientation of FIG. 9b. In this way the external surface 50 of the apparatus abuts the vertebrae as the apparatus is rotated, with continued rotation increasing the separation of the vertebrae to the desired level where the device can be introduced easily. The separation of the vertebrae may be assisted by the use of spreader blocks.

In addition to the above mentioned technique in which the device is straightened and then restrained during insertion to maintain it in the linear profile, it is possible to make use of the different properties of shape memory alloys in their respective cold state and warm state. In the warm state it is possible to straighten and physically restrain in a position a normally curved strip. If the temperature of the strip is then reduced, the deformation can be fixed using the cold state for the shape memory alloy. In this cold state the device can then be introduced into the intervertebral disc space, with the warmth of the body into which the device is inserted causing the device to warm up once more and pass from the cold state to warm state, whereupon the device assumes its original curved configuration. The warming process can be assisted beneficially by external heating of the device. The device may be heated up to between 40° C. and 50° C. and then allowed to cool. The hysteresis curve for the memory metal gives benefits in such a case.

Whilst the invention is particularly concerned with the use of shape memory alloys to achieve the desired balance of flexibility and support in a spinal fusion device, some of the benefits of the invention can be obtained through the use of carefully configured conventional materials, i.e. elastic materials. To achieve the aim of inserting the device through a small insert in the spine the device, FIG. 10, is once again provided in the form of a strip 100 which assumes a U-shaped profile in use. To achieve the desired level of support in use from such materials a significant upper and lower surface area needs to be provided. With conventional material, however, this results in a strip which is insufficiently flexible to be placed in a linear, pre-dispensed form, if a single piece of material is used. To overcome this the device in this embodiment is formed of a series of thinner strips 102 which are joined together by fixing piece 104 at one end. In use this is the end which is inserted into the patient first. The thicknesses of the individual strips and their ability to move relative to one another allows them the desired degree of flexibility.

In the various embodiments as described above a single device is inserted between a pair of vertebrae to facilitate fusion thereof. In some cases, such as osteoporosis, a greater level of bearing surface needs to be provided and this can be achieved using the present invention through two or more devices being deployed between a pair of vertebrae. Three potential configurations for such deployments are illustrated in FIGS. 11a, 11b and 11c. In each case the main aim of minimum invasion is achieved. In FIG. 11a the two devices 200 are provided in the same configuration, but alongside one another. In the FIG. 11b situation the two devices 200 are provided with a part of each device within the outline of the other. In the FIG. 11c situation one of the devices 200 is used to obstruct the gap between the two ends of the other device 200. Configurations such as this mechanically assist the retention of bone graft material in the fusion site.

Whilst the device can readily be used using apparatus, such as that illustrated in FIG. 4, which facilitates insertion only of the device. It may be desirable in some cases, however, to be able to manipulate the device after insertion and/or to remove it. This may even include removal of the device from the spine entirely by retracting it into the apparatus. This may cause the device to assume the first state once more, from the second state. To this end FIG. 12 illustrates a modified end portion 300 for a device 302 of the type described above, and a cooperating part 304 of the dispensing apparatus.

The end portion 300 of the device 302 has a recess with a reduced width portion 306 and expanded width portion 308 which together form a dove tail. The maximum width of the portion 308 is less than the normal width 310 of the device 300 so as not to increase the extent of invasion during surgery. By providing a corresponding protrusion 312 to the dove tail in the cooperating part 304 of the dispensing apparatus a good engagement between the two can be provided.

As described above, advancing the driving part of the apparatus causes the device 302, during implantation, to be advanced into the patient, by means of the cooperating part 304 and dove tail cooperation. If the surgeon wishes to retract the device 302, however, that is possible using this type of cooperation as any retraction of the cooperating part 304 of the device results in withdrawal of the device 302. This may even include transferring the device from the second state back to the first state by withdrawing it entirely to within the surgical apparatus. Similarly manipulative movements can be conveyed from the apparatus to the cooperating part 304 and hence to the device 302 in the patient.

Various means, from simply moving the whole apparatus to retracting the cooperating part 304 into the apparatus, can be used to effect the retraction and/or manipulation of the device 302.

From the foregoing embodiments it should be clear that the invention provides a device which can have a large transverse dimension, so that the fitting of one such device in an intervertebral space should be able to suffice, it being possible for said device to be fitted through a relatively narrow slit and with a less drastic surgical intervention. It should also be clear that the device is constituted by a strip of memory material which may be curved in various ways, in which connection only a few of the possible embodiments are shown above by way of illustration. The term device should be taken as potentially interchangeable with the term prosthesis.

What is claimed is:

1. An intervertebral fusion device, the device having a single component comprising an elongate element, the elongate element providing one or more upper load bearing surfaces and one or more lower load bearing surfaces, to be engaged by respective vertebrae in use, the upper and lower load bearing surfaces being vertically spaced from one another by the elongate element, and the elongate element being rigid in a direction parallel to the vertical spacing of the upper and lower load bearing surfaces, the elongate element having a first state and a second state, the elongate element having a substantially linear configuration in the first state and a less linear configuration in the second state, the elongate element being capable of transition, at least once, from the second state to the first state and being capable of transition, at least once, from the first state to the second state, the elongate element being of shape memory alloy.

2. A fusion device according to claim 1, in which the first state provides a linear configuration for the elongate element.

3. A fusion device according to claim 1, in which the first state provides a configuration in which one end of the elongate element is further from the other end of the elongate element, measured along a straight line, than from any other part of the elongate element, the device having a waveform configuration.

4. A fusion device according to claim 1, in which the second state provides a configuration in which at least a part of the elongate element is curved.

5. A fusion device according to claim 1 in which the second state provides a configuration in which at least part of the elongate element is provided as a waveform and/or undulating strip.

6. A fusion device according to claim 1 in which in the second state the elongate element has a configuration which is a part circle and/or full circle and/or spiral and/or U-shape and/or a part oval and/or full oval.

7. A fusion device according to claim 1 in which the elongate element has a different thickness at one or more locations along its length than at other locations along its length, the reduced thickness locations extend across the full width of the elongate element.

8. A fusion device according to claim 7 in which the reduced thickness locations are provided by grooves in the elongate element.

9. A fusion device according to claim 7 in which the reduced thickness portions are preferentially provided in the portion or portions of the elongate element which undergo a change in profile during the transition from first to second state compared with the portion or portions of the elongate element which undergo no or a lesser change in profile during the transition from the first to second state.

10. A fusion device according to claim 1 in which the elongate element has a thickness of less than 3 mm.

11. A fusion device according to claim 1 in which the maximum extent of the elongate element, measured from any point to any other in a straight line, is less than 50 mm, when considered in the second state.

12. A fusion device according to claim 1 in which the elongate element has a non-rectilinear cross section at one or more locations along its length, a rectilinear cross section being provided at a location between those locations of non-rectilinear cross section.

13. A fusion device according to claim 12 in which the non-rectilinear cross section provides an increased thickness portion at the upper load bearing surface and at the lower load bearing surface of the elongate element.

14. A fusion device according to claim 1 in which the elongate element has an upper load bearing surface or surfaces and a lower load bearing surface or surfaces, the upper and lower load bearing surface and/or one or more of the upper and lower load bearing surfaces being parallel to one another.

15. A fusion device according to claim 14 in which the vertical spacing of the upper and lower load bearing surface or surfaces is between 7 mm and 20 mm.

16. A fusion device according to claim 14 in which the minimum vertical spacing is more than 4 mm.

17. A fusion device according to claim 1 in which the elongate element has an upper load bearing surface or surfaces and/or a lower load bearing surface or surfaces which are provided with serrations or spikes.

18. A fusion device according to claim 1 in which the upper and lower load bearing surface and/or one or more of the upper and lower load bearing surfaces are angled relative to one another, the angle between a projection of the upper load bearing surfaces and/or at least one of the upper load bearing surfaces and the lower load bearing surface and/or at least one of the lower load bearing surfaces, the angle being 5° to 15°.

19. A fusion device according to claim 1 in which the elongate element has one or more holes in it, the holes being round and/or oval and/or triangular and/or diamond shaped.

20. A fusion device according to claim 1 in which at least one end of the elongate element is provided with an engagement profile, the engagement profile defining a dovetail.

21. A method of surgery, the method including the acts of:
making an incision in the patient; removing at least part of an intervertebral disc from the patient though the incision, thereby providing an intervertebral disc space; and
inserting a device into the intervertebral space; the device having a single component comprising an elongate element, the elongate element providing one or more upper load bearing surfaces for a vertebrae and one or more lower load bearing surfaces for a vertebrae, the upper and lower load bearing surfaces being engaged by respective vertebrae in use, the upper and lower load bearing surfaces being vertically spaced from one another by the elongate element and the elongate element being rigid in a direction parallel to the vertical spacing of the upper and lower load bearing surfaces, the elongate element having a first state prior to insertion and a second state after insertion, the elongate element having a substantially linear configuration in the first state and a less linear configuration in the second state, the elongate element being capable of transition, at least once, from the second state to first state and being capable of transition, at least once, from the first state to the second state, the elongate element being of shape memory alloy.

22. A method according to claim 21 in which the shape memory alloy of the device is in a cold state in the first state and is in a warm state in the second state, the device being warmed, at least in part by the body heat of the patient, the warming causing the transition from cold to warm state for the memory metal of the device and hence from the first to the second state of the device.

23. A method according to claim 22 in which external heating of the device is applied, the temperature of the device in the patient being raised to at least 40 C.

24. An intervertebral fusion device, the device having a single component comprising an elongate element, the elongate element providing one or more upper load bearing surfaces and one or more lower load bearing surfaces to be engaged by respective vertebrae in use, the upper and lower load bearing surfaces being vertically spaced from one another by the elongate element and the elongate element being rigid in a direction parallel to the vertical spacing of the upper and lower load bearing surfaces, the elongate element having a first state and a second state, the elongate element having a substantially linear configuration in the first state and a less linear configuration in the second state, the elongate element being capable of transition, at least once, from the second state to first state and being capable of transition, at least once, from the first state to the second state, the elongate element being formed of a plurality of elongate components which at least in part extend alongside one another.

25. A fusion device according to claim 24 in which the elongate components (102) correspond to one another in form.

26. A fusion device according to claim 24 in which the elongate components are in the form of a plurality of equivalently configured strips, adjacent strips being in contact with one another.

27. A fusion device according to claim 24 in which the elongate components are connected together to form a single elongate element, the elongate components being connected together at one end.

28. An intervertebral fusion device, the device being a single component comprising a memory metal elongate element, the elongate element providing one or more upper load bearing surfaces and one or more lower load bearing surfaces for engaging respective vertebrae in use and being vertically spaced from one another by the elongate element, the elongate element being rigid in a directional parallel to the vertical spacing of the upper and lower load bearing surfaces having first and second ends and a substantially non-linear configuration between the two ends.

29. A fusion device according to claim 28 wherein the elongate element has a thickness and the substantially non-linear configuration defines a radius, and wherein the thickness and radius are predetermined so that, when the elongate element is straightened to form a substantially linear configuration, no deformations of more than 8% arise.

30. A fusion device according to claim 28 wherein the ratio of the radius to the thickness is at least 8:1.

31. A method of using a prosthetic device, comprising the steps of:
a) providing an intervertebral fusion device, the device being a single component comprising a memory metal elongate element, the elongate element providing one or more upper load bearing surfaces and one or more lower load bearing surfaces for engaging respective vertebrae in use and being vertically spaced from one another by the elongate element, the elongate element being rigid in a directional parallel to the vertical spacing of the upper and lower load bearing surfaces having first and second ends and a substantially non-linear configuration between the two ends;
b) straightening the non-linear configuration of the elongate element to form a substantially linear configuration;
c) inserting the straightened device into the disc space, and
d) curving the substantially linear configuration of the elongate element to reform the non-linear configuration.

* * * * *

UNITED STATES PATENT AND TRADEMARK OFFICE
CERTIFICATE OF CORRECTION

PATENT NO. : 6,656,178 B1  Page 1 of 1
DATED : December 2, 2003
INVENTOR(S) : Veldhuizen et al.

It is certified that error appears in the above-identified patent and that said Letters Patent is hereby corrected as shown below:

Column 3,
Line 40, "one or" should read -- one or more --.
Line 54, "various" should read -- varying --.

Column 5,
Line 20, "device. the" should read -- device. The --.

Column 7,
Line 6, "embodiment" should read -- embodiment, --.
Line 48, 49, & 51, "device's" should read -- devices --.
Line 63, "increase the" should read -- increases the --.

Column 8,
Line 5, "part be caused" should read -- part caused --.

Column 9,
Line 36, "the holing" should read -- the holding --.
Line 57, "has" should read -- with --.
Line 60, "strip are" should read -- strip --.

Column 12,
Line 48, "ensures" should read -- ensure --.

Column 14,
Line 49, "spine the" should read -- spine, the --.

Signed and Sealed this

Eighth Day of June, 2004

JON W. DUDAS
*Acting Director of the United States Patent and Trademark Office*